Figure 1:
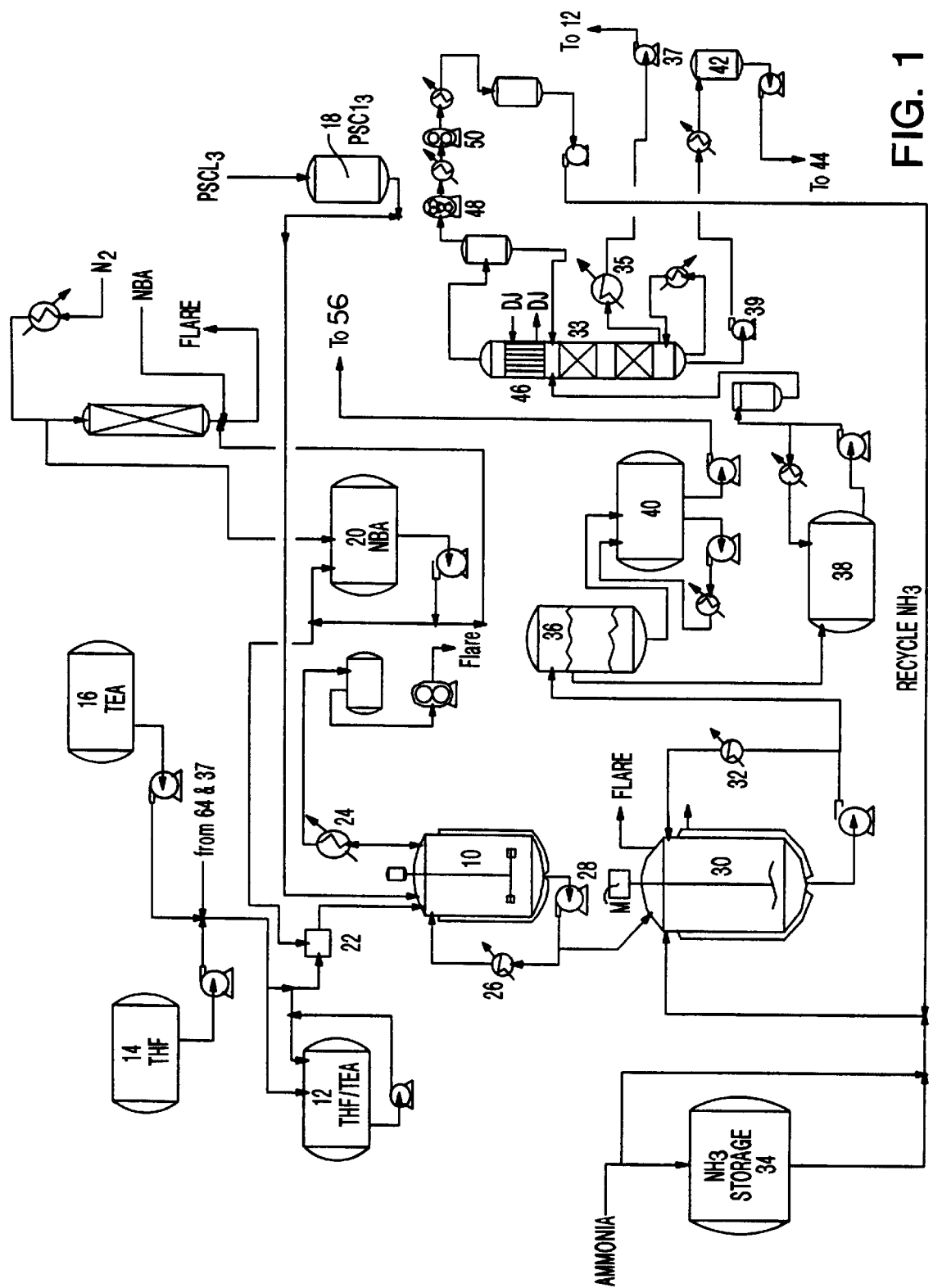

US005871667A

United States Patent [19]
Cheng et al.

[11] Patent Number: 5,871,667
[45] Date of Patent: Feb. 16, 1999

[54] INHIBITING FERROUS METAL CORROSION BY AQUEOUS AMMONIATE SOLUTIONS

[75] Inventors: Chi Hung Cheng; Gerald M. Sulzer, both of Baton Rouge, La.

[73] Assignee: Albemarle Corporation, Richmond, Va.

[21] Appl. No.: 786,536

[22] Filed: Jan. 21, 1997

[51] Int. Cl.$^6$ .............. C07F 9/22; C01C 1/16; C01C 1/28

[52] U.S. Cl. .............. 252/389.52; 252/389.22; 252/389.62; 252/391; 71/29; 71/30; 422/12; 562/809; 562/813; 562/814; 564/14; 568/14

[58] Field of Search .............. 252/389.21, 389.22, 252/389.23, 389.62, 389.52, 391; 422/13, 15, 12, 19; 71/29, 61, 28; 564/14; 562/809, 813, 814; 568/14

[56] References Cited

U.S. PATENT DOCUMENTS

| | | | |
|---|---|---|---|
| 2,220,059 | 11/1940 | Beekhuis et al. | 23/239 |
| 2,613,131 | 10/1952 | Barnes et al. | 23/1 |
| 2,957,762 | 10/1960 | Young | 71/59 |
| 3,168,392 | 2/1965 | Creech | 71/59 |
| 3,197,496 | 7/1965 | LeSuer | 260/461 |
| 3,309,317 | 3/1967 | Wittner et al. | 252/49.9 |
| 3,531,550 | 9/1970 | Herber et al. | 260/959 |
| 3,615,290 | 10/1971 | Nixon | 44/51 |
| 3,933,907 | 1/1976 | Ashton et al. | 260/551 P |
| 4,210,437 | 7/1980 | Windgassen et al. | 71/28 |
| 4,242,325 | 12/1980 | Bayless et al. | 424/210 |
| 4,256,691 | 3/1981 | Ott | 422/7 |
| 4,530,714 | 7/1985 | Kolc et al. | 71/28 |
| 4,629,491 | 12/1986 | Swerdloff et al. | 71/87 |
| 5,616,769 | 4/1997 | Sakito et al. | 558/146 |
| 5,770,771 | 6/1998 | Sulzer et al. | 564/14 |

FOREIGN PATENT DOCUMENTS

| | | |
|---|---|---|
| 1314310 | 4/1963 | France . |
| 0909882 | 3/1954 | Germany . |
| 830800 | 3/1960 | United Kingdom . |
| 848952 | 9/1960 | United Kingdom . |

OTHER PUBLICATIONS

L.A. Cates; "Phosphorus–Nitrogen Compounds. XL. Phosphamidase Studies. I. Unsubstituted Amides[1,2]", J. Med Chem., vol. 13, 1970; pp. 301–302.

M. Goehring, et al.; "Uber Phosphor–Stickstoffverbindungen, I. Mitteil.: Zur Kenntnis der Amide der Phosphorsaure und der Thiophosphorsaure"; Chem. Ber., No. 7, 1956; pp. 1768–1774 (untranslated).

Kendall, et al; "Addition Compounds of Ammonia With The Ammonium Halides"; J. Amer. Chem. Soc., 1920, vol. 42; pp. 1141–1145.

Yamamoto, et al., "Measurement of Heat of Mixing for Ammonium Chloride + Ammonia System at 25° C."; The Canadian Journal of Chemical Engineering, vol. 66, 1988; ppp. 127–130.

Abe, et al., "Regarding The Solubility of Di– And Trichlorides In Liquid Ammonia (Part 3) Solubility Of Ammonium Chloride And Vapor Pressure Of Its Solution"; 1935; J. Soc. Chem. Ind. Japan, vol. 38; pp. 1402–1406.

*Primary Examiner*—Joseph K. McKane
*Assistant Examiner*—Deanna Baxam
*Attorney, Agent, or Firm*—Philip M. Pippenger

[57] ABSTRACT

Aqueous ammoniate solutions made during the manufacture of N-hydrocarbyl thiophosphoric triamides, consisting essentially of aqueous solutions of ammonium chloride and ammonia containing a water-soluble impurity normally tending to engender corrosion of ferrous metal are rendered corrosion-resistant by dissolving therein a small corrosion-inhibiting amount (e.g., up to about 5000 ppm (wt/wt) of a water-soluble salt or oxide of zinc, aluminum, arsenic, antimony or bismuth.

20 Claims, 2 Drawing Sheets

INHIBITING FERROUS METAL CORROSION BY AQUEOUS AMMONIATE SOLUTIONS

BACKGROUND

N-hydrocarbylthiophosphoric triamides are known to be effective urease inhibitors for use with urea-based fertilizer compositions. See, for example, U.S. Pat. No. 4,530,714 to J. F. Kolc, et al.

Known procedures for preparing such triamides involve operations in which N-hydrocarbylaminothiophosphoryl dichloride (also known as N-hydrocarbylthiophoramidic dichloride) is formed in a first reaction, recovered, and often purified. In a second reaction, the N-hydrocarbylaminothiophosphoryl dichloride is reacted with ammonia to produce a slurry from which co-product ammonium chloride is separated by filtration. See for example, U.S. Pat. No. 4,530,714.

In commonly-owned copending U.S. applications Ser. Nos. 08/786,396 now U.S. Pat. No. 5,770,771, 08/786,535, and 08/785,104, all filed Jan. 21, 1997,—all disclosures of which are incorporated herein in toto by reference—new, highly advantageous process technology is described for co-producing N-hydrocarbylthiophosphoric triamides and aqueous ammoniate solutions. These ammoniate co-product solutions formed in the processing and are chiefly composed of ammonia and ammonium chloride.

While solutions of ammonia and ammonium chloride made from essentially pure ammonia and ammonium chloride do not cause significant ferrous metal corrosion, it has been found that aqueous ammoniate solutions made in accordance with some of the process technology of the aforesaid applications do tend to cause such corrosion, at least in the case of mild steel. It appears therefore that trace amounts of impurities carried over from the processing is responsible for such corrosion, and since the processing typically involves use of thiophosphoryl chloride ($PSCl_3$) as an initial starting material, it is reasonable to believe that trace amounts of some currently unidentified sulfur-containing impurities are the cause of the corrosion.

A very desirable contribution to the art would be the discovery of an effective way of inhibiting such corrosion without at the same time requiring use of expensive and/or time-consuming purification procedures.

This invention is deemed to have fulfilled this need.

THE INVENTION

In accordance with this invention, certain substances have been found to be highly effective in inhibiting the aforesaid corrosion of ferrous metal such as mild steel. These inhibitors are relatively inexpensive and can be effectively employed in small amounts (e.g. up to about 5000 ppm (wt/wt) in the ammoniate solutions and thus their presence does not interfere with the usefulness of these industrially useful solutions. Moreover tests have indicated that the inhibitors used are effective in the ammoniate solutions for long periods of time. Accordingly it is now possible to store and transport the inhibited ammoniate solutions in ferrous metal equipment such as railroad tank cars, tank trailer trucks, drums, pipelines, storage tanks, and the like, without encountering excessive ferrous metal corrosion.

The inhibitors of the present invention are water-soluble salts or oxides of zinc, aluminum, arsenic, antimony or bismuth. These inhibitors may be used singly or in combinations of two or more such materials. The inhibitors are used in ferrous metal corrosion-inhibiting amounts which typically are no more than about 5000 ppm (wt/wt) and preferably no more than about 1000 ppm (wt/wt) in the aqueous ammoniate solutions. By water-soluble is meant that the salt or oxide will dissolve at 25° C. in the aqueous ammoniate solution in an amount at least sufficient to inhibit ferrous metal corrosion so that the solution containing the inhibitor produces less ferrous metal corrosion than the same aqueous ammoniate solution into which no such inhibitor has been blended. Thus there is no requirement that the inhibitor be soluble in all proportions in the aqueous ammoniate solution to be inhibited thereby. Indeed, in many cases, the solubility of the inhibitor in water will be relatively low, yet sufficient for the purposes at hand. Generally speaking a solubility in water of at least 1000 ppm (wt/wt) at 25° C. is sufficient.

Aqueous ammoniate solutions to which this invention is applicable are those comprising in the range of about 10 to about 50 wt % of ammonia and in the range of about 10 to about 50 wt % of ammonium chloride with the balance being water and one or more water-soluble impurities normally tending to engender corrosion of ferrous metal when the solution is in contact therewith, especially for long periods of time (e.g., 30 days or longer). Preferred aqueous ammoniate solutions contain in the range of about 15 to about 40 wt % of ammonia and in the range of about 15 to about 40 wt % of ammonium chloride with the balance being water and one or more of such water-soluble corrosion-inducing impurities.

The rate of corrosion engendered by such impurities appears to be increased when the ferrous metal is exposed to air during or after contact with the aqueous ammoniate solution. Yet the inhibitors of this invention effectively inhibit the corrosion, even under these severe service conditions.

In accordance with one embodiment of this invention there is provided an aqueous solution of ammonium chloride and ammonia containing at least one water-soluble impurity normally tending to promote corrosion of ferrous metal, which solution additionally has dissolved therein a ferrous metal corrosion-inhibiting amount of at least one water-soluble salt or oxide of zinc, aluminum, arsenic, antimony or bismuth.

Another embodiment of this invention is a process of inhibiting ferrous metal corrosion during contact with an aqueous solution of ammonium chloride and ammonia containing at least one water-soluble impurity normally tending to engender corrosion of ferrous metal, which process comprises blending with such solution a ferrous metal corrosion-inhibiting amount of at least one water-soluble salt or oxide of zinc, aluminum, arsenic, antimony or bismuth. As noted above, this process effectively inhibits the ferrous metal corrosion occurring even when the ferrous metal is also in contact concurrently or subsequently with air.

Another embodiment of this invention is a process which comprises:

a) mixing and reacting a hydrocarbyl primary amine and thiophosphoryl chloride, preferably in at least one liquid inert organic solvent and in the presence of tertiary amine to complex with the HCl formed in the reaction, and most preferably maintaining the temperature of the reaction mixture in the range of about −20° to about +50° C., to produce a reaction mixture containing N-hydrocarbylaminothiophosphoryl dichloride;

b) mixing and reacting ammonia and at least a portion of the reaction mixture formed in a) in proportions (1) that are at least about 16 moles of ammonia per mole of N-hydrocarbylaminothiophosphoryl dichloride, (2) that produce a reaction mixture containing N-hydrocarbylthiophosphoric triamide, and (3) that keep in solution substantially all of the ammonium chloride co-product formed in the reaction, and maintaining the temperature of the reaction mixture high enough to keep ammonium chloride-ammonia complex from forming an appreciable amount of solid phase in said reaction mixture, but low enough to avoid significant reduction in yield of N-hydrocarbylthiophosphoric triamide;

c) allowing/causing the reaction mixture of b) to form an anhydrous predominately inorganic liquid phase comprising ammonia and ammonium chloride and/or a product or complex thereof, and a separate anhydrous predominately organic liquid phase comprising N-hydrocarbylthiophosphoric triamide and, if used, said solvent;

d) separating said phases from each other; and e) converting at least a portion of the separated predominately inorganic liquid phase into a corrosion-inhibited aqueous solution thereof by adding to the water used in forming such solution or by adding to said solution after it has been formed, a ferrous metal corrosion-inhibiting amount of at least one water-soluble ferrous metal corrosion inhibitor selected from a salt or an oxide of zinc, aluminum, arsenic, antimony or bismuth.

For ease of reference, the separate liquid phase containing the ammonia and the ammonium chloride is sometimes referred to hereinafter as the ammoniate phase.

It has been found that the ammoniate phase (which is predominately inorganic) and the remainder of the initial mixture (which is predominately organic) are easily separated from each other, for example by a gravity separation (e.g., draining off the lower layer or by siphoning or otherwise drawing off the upper layer), or by use of other known procedures for separating one liquid phase from another.

A preferred process comprises:

a) continuously feeding to and mixing in a first reaction chamber (i) a preformed mixture of primary hydrocarbyl monoamine (preferably a monoalkyl monoamine, such as n-butylamine), tertiary amine (preferably a trialkylamine such as triethylamine) and at least one liquid inert organic solvent (preferably a cyclic ether such as tetrahydrofuran), and (ii) thiophosphoryl chloride and removing heat of reaction at a rate sufficient to maintain the temperature of the reaction mixture in the range of about −20° to about +50° C., produce a reaction mixture containing N-hydrocarbylaminothiophosphoryl dichloride;

b) continuously feeding and mixing in a second reaction chamber (i) an effluent stream of reaction mixture formed in the first reaction chamber which effluent is withdrawn at a rate to maintain a substantially constant volume of reaction mixture in the first reaction chamber, and (ii) ammonia in proportions (1) that are at least about 16 moles of ammonia per mole of N-hydrocarbylaminothiophosphoryl dichloride, (2) that produce a reaction mixture containing N-hydrocarbylthiophosphoric triamide, and (3) that keep in solution substantially all of the ammonium chloride co-product formed in the reaction, and removing heat of reaction from the mixture formed in b) at a rate of removal such that the temperature of the reaction mixture remains high enough to keep ammonium chloride-ammonia complex from forming an appreciable amount of solid phase in said reaction mixture, but low enough to avoid significant reduction in yield of N-hydrocarbylthiophosphoric triamide;

c) withdrawing effluent from the second reaction chamber at a rate sufficient to maintain a substantially constant volume of reaction mixture in the second reaction chamber;

d) enabling/causing the effluent from c) to separate into a predominately inorganic liquid phase comprising predominately ammonia, ammonium chloride and co-product thiophosphoric triamide, and a predominately organic liquid phase comprising predominately N-hydrocarbylthiophosphoric triamide, tertiary amine, solvent and dissolved ammonia;

e) separating the resultant phases from each other; and f) converting at least a portion of the separated predominately inorganic liquid phase into a corrosion-inhibited aqueous solution thereof by adding to the water used in forming such solution or by adding to said solution after it has been formed, a ferrous metal corrosion-inhibiting amount of at least one water-soluble ferrous metal corrosion inhibitor selected from a salt or an oxide of zinc, aluminum, arsenic, antimony or bismuth.

The temperature of the reaction mixture in step b) above in which the triamide and ammonium chloride are being co-produced by reaction between (i) N-hydrocarbylaminothiophosphoryl dichloride and (ii) a suitable amount of initially added and/or incrementally added ammonia, should be maintained above about 6° C. but below the temperature at which the triamide undergoes significant thermal degradation. At temperatures of about 6° C. and below, an ammonia-ammonium chloride complex of some sort tends to form as a solid phase which can cause pluggage of reaction equipment and which in any event detracts from the efficiency of the overall operation. Thus such low temperatures should be avoided. The thermal degradation temperatures of the triamides usually differs at least to some extent from compound to compound, and thus the maximum permissible temperature may vary from compound to compound. In general, however, significant thermal degradation of the triamides is not incurred at temperatures of up to about 50° C. and in some cases perhaps not until up to still higher temperatures.

The above and other embodiments of this invention will be still further apparent from the ensuing description, accompanying drawings, and appended claims.

THE DRAWINGS

Figure 2:
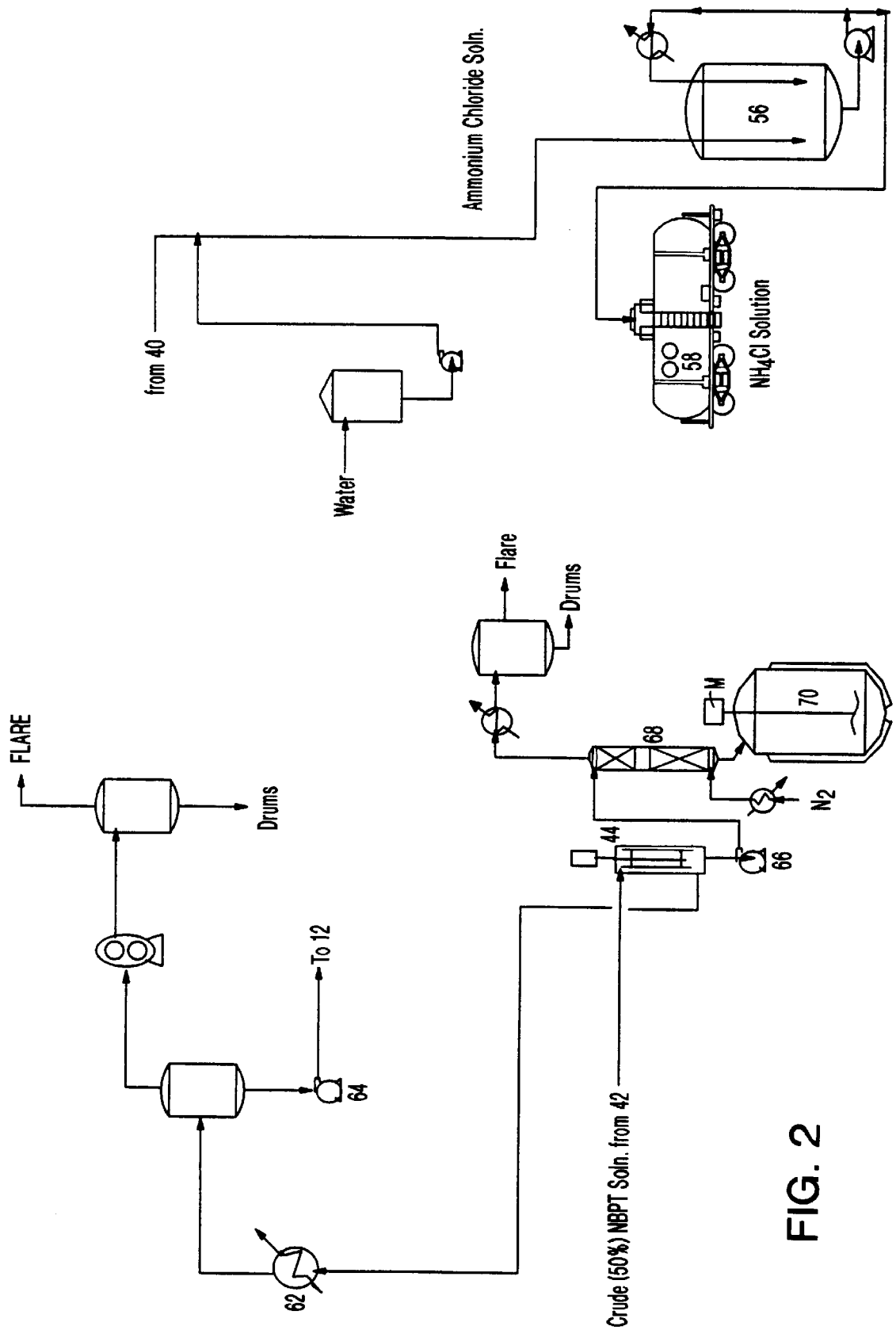

FIGS. 1 and 2, taken together, constitute a schematic representation of a preferred overall installation and the process flows for the production and purification of N-hydrocarbylaminothiophosphoryl dichloride on a continuous basis. In such processing an ammoniate phase is formed and typically is converted into an aqueous solution which is inhibited against ferrous metal corrosion pursuant to this invention.

FIG. 1 schematically depicts the preferred installation and flow streams for the two-stage reactions used in the process.

FIG. 2 schematically depicts the preferred installation and flow streams for the workup and recovery of products formed in the operation of the installation of FIG. 1.

FURTHER DETAILED DESCRIPTION

Suitable salts for use as corrosion inhibitors pursuant to this invention include the halides, nitrates, phosphates, oxyhalides, hydroxides, and like salts which preferably are sulfur-free. A few examples of candidate salts include bismuth hydroxide, bismuth tribromide, bismuth oxybromide, bismuth monochloride, bismuth dichloride, bismuth trichloride, bismuth oxychloride, bismuth trifluoride, bismuth iodate, bismuth oxyfluoride, bismuth triiodide, bismuth oxyiodide, bismuth nitrate, bismuth phosphate, bismuth arsenate, bismuth citrate, bismuth lactate, bismuth oxalate, zinc hydroxide, zinc oxalate, zinc dibromide, zinc dichloride, zinc perchlorate, zinc cyanide, zinc ferrocyanide, zinc difluoride, zinc diiodide, zinc nitrate, zinc phosphate, zinc acetate, zinc benzoate, zinc borate, zinc bromate, zinc caproate, zinc chlorate, zinc dichromate, zinc citrate, zinc fluosilicate, zinc formate, zinc iodate, zinc lactate, zinc tartrate, aluminum bromate, aluminum bromide, aluminum chlorate, aluminum chloride, aluminum fluoride, aluminum hydroxide, aluminum iodide, aluminum nitrate, aluminum phosphate, aluminum acetate, aluminum ferrocyanide, aluminum lactate, aluminum silicate, arsenic pentafluoride, arsenic pentaiodide, arsenic tribromide, arsenic trichloride, arsenic triiodide, arsenic oxychloride, antimony tribromide, antimony trichloride, antimony pentachloride, antimony trifluoride, antimony pentafluoride, antimony oxychloride, and antimony d-tartrate. Candidate oxides include, for example, $Bi_2O_3$, $Bi_2O_5$, ZnO, $ZnO_2$, $Al_2O_3$, $As_2O_3$, $As_2O_5$, $Sb_2O_3$, $Sb_2O_4$, and $Sb_2O_5$. The salts and the oxides as added to the aqueous ammoniate solution may contain water of hydration. On addition to the aqueous ammoniate solution, the salts and/or oxides may be converted in situ (e.g., through ionization, solvation, hydrolysis, and/or other chemical reaction, etc.) into other forms or compounds, and this is within the purview and scope of this invention, provided the transformed form or composition of the added salt or oxide remains in solution and exerts a corrosion inhibiting effect with respect to the ferrous metal to which the resultant ammoniate solution is exposed. Thus the description herein of oxide and salt additives refers to the chemical composition (except for permissible water of hydration) of the oxide or salt before it comes into contact with the water or aqueous ammoniate solution. In this connection the oxide or salt may be added to the water used in forming the ammoniate solution or the oxide or salt may be added to the ammoniate solution during its formation or after it has been formed. Combinations of such modes of addition can also be used if desired. Preferably the oxide or salt is blended with the aqueous ammoniate solution shortly after it has been formed. The oxide or salt can be added in the form of a preformed concentrated solution in water or other suitably innocuous solvent such as a water-soluble ether (e.g. tetrahydrofuran) or alcohol (e.g., methanol, ethanol, or 2-propanol) in order to facilitate the blending operation.

Preferred corrosion inhibitor additives are one or more of the following: zinc oxide, a zinc dihalide, aluminum oxide, an aluminum trihalide, bismuth oxide. Particularly preferred are ZnO, $ZnCl_2$, $Al_2O_3$, $AlCl_3$, and $Bi_2O_3$.

The results of comparative experiments set forth in the following illustrative Example demonstrate the effectiveness and advantages derivable by the practice of this invention. This Example is not intended to limit the scope of this invention.

EXAMPLE

Several tests were carried out using either synthetic ammoniate solution or an aged ammoniate solution. The aged ammoniate solution was generated by use of a process similar to that described hereinafter with reference to the continuous process two-stage process for producing N-hydrocarbylthiophosphoric triamides starting with $PSCl_3$ as one of the starting materials. The ammoniate solution had been stored in a mild steel tank car for several months before the tests were conducted. Mild steel coupons were placed in samples of the aqueous ammoniate solution containing 40–50% by weight of ammoniate, and tested at ambient temperature. Samples in which oxides or salts were added to the ammoniate solution were also included in these tests. The corrosion rate was measured based on the weight loss vs. time the coupons remained immersed in the respective solutions. It was found that the corrosion rate of mild steel was reduced from about 4 mils per year to less than 0.3 mil per year when about 1000 ppm of $Bi_2O_3$, ZnO, $ZnCl_2$, $AlCl_3$, or $Al_2O_3$ was incorporated into the solution. In similar comparative tests wherein zinc chloride was the additive used, the coupons were alternately dipped in the ammoniate solution and exposed to air. In this case, the corrosion rate of the mild steel was reduced from a rate of about 36 mils per year when no corrosion inhibitor additive was employed, to about 13 mils per year when 1000 ppm (wt/wt) $ZnCl_2$ was added to the sample of aged ammoniate solution. In other tests it was found that a synthetic solution made from commercially pure $NH_3$, $NH_4Cl$, and water was not corrosive to the mild steel coupons, thus indicating that the corrosion experienced with the aged ammoniate solution was due to some sulfur impurities (e.g. sulfide, sulfate) in the solution.

When producing N-hydrocarbylthiophosphoric triamides it is most desirable to utilize a continuous process to produce the triamide and to include in the overall operation use of a corrosion inhibitor in an aqueous ammoniate solution pursuant to this invention. The continuous process is described in commonly-owned copending U.S. application Ser. No. 08/786,396, filed Jan. 21, 1997, all disclosure of which is incorporated herein by reference.

Continuous Process

The ensuing description focuses primarily on the embodiments wherein the N-hydrocarbylaminothiophosphoryl dichloride and the N-hydrocarbylthiophosphoric triamide are both formed in a continuous process.

Reactants. The principal reactants in the continuous process are primary hydrocarbyl monoamine, thiophosphoryl chloride ($PSCl_3$), and ammonia. The hydrocarbyl group of the primary amine reactant can be any hydrocarbyl group such as alkyl, cycloalkyl, alkenyl, cycloalkenyl, alkynyl, aryl, aralkyl, or cycloalkylalkyl group. Typically the hydrocarbyl group will contain up to about 20 carbon atoms, and preferably up to about 10 carbon atoms. Of such compounds monoalkyl amines, monocycloalkylamines and monoarylamines are preferred, and of these, monoalkyl amines having 2 to 6 carbon atoms in the molecule are especially preferred. Most preferred as the amine reactant is n-butylamine.

The ammonia is preferably stored and handled in its liquid form. However, gaseous ammonia, or mixtures of gaseous and liquid ammonia, can also be used, if desired.

Solvent. As noted above, at least one liquid inert organic solvent is employed in the process. While any solvent meeting these criteria can be used, it is preferred to use a solvent that boils at one or more temperatures in the range of about 40° to about 120° C. and preferably in the range of about 55° to about 90° C. at ordinary atmospheric pressures. Thus use can be made of liquid paraffinic, cycloparaffinic, and/or aromatic hydrocarbons, liquid halocarbons and halohydrocarbons, ethers, esters, and other organic liquids which do not interfere with the desired reactions. Ethers, especially cyclic ethers such as 1,4-dioxane, 1,3-dioxolane, tetrahydrofuran, methyltetrahydrofuran, and tetrahydropyran, are preferred. Preferably the solvent is recovered, most preferably by one or more flash distillations, and is used as recycle in the process.

Of the various suitable solvents, tetrahydrofuran is particularly preferred because of its good solvency properties, desirable boiling point, ready availability and low cost. In a well-designed facility for the process of this invention, about 99% of the tetrahydrofuran can be recovered, and preferably the recovered tetrahydrofuran is used as recycle in the process.

HCl Acceptor. A tertiary amine is used as an acid acceptor for the by-product HCl formed in the first reaction. It is not consumed by the process, and in the preferred embodiments the tertiary amine is recycled in the process. Suitable tertiary amines include heterocyclic tertiary amines such as 3-picoline (bp ca. 143°–144° C.), 4-picoline (bp ca. 143° C.), 4-chloropyridine (bp ca. 147°–148° C.), 3-ethylpyridine (bp ca. 165°–166° C.), and 4-ethylpyridine (bp ca. 166° C.), and trialkylamines such as tripropylamine (bp ca. 155°–158° C.), and tri-sec-butylamine (bp ca. 191°–192° C.). Relatively low boiling tertiary amines such as pyridine (bp ca. 115° C.), 2-picoline (bp ca. 128° C.), N,N-diethylmethylamine (bp 63°–65° C.), and triethylamine (bp ca. 89° C.) are preferred.

From a cost-effectiveness standpoint, triethylamine is a particularly preferred tertiary amine. In a well-designed facility for the continuous process, about 99% of the triethylamine can be recovered, and preferably the recovered triethylamine is used as recycle in the process. Thus the process is capable of producing suitably high purity product (s) while at the same time being both highly efficient and environmentally friendly.

Reaction Conditions. The first stage reaction involving reaction between thiophosphoryl chloride and the primary amine is typically conducted at one or more temperatures in the range of about −20° to about 50° C., and preferably at one or more temperatures in the range of about 0° to about 15° C. The pressure conditions for this reaction are not important unless evaporative cooling is used to control reactor temperature. If using evaporative cooling, the reactor pressure is controlled such that the reaction mass will boil at the reactor temperature. Proportions of reactants in the first stage are essentially equimolar, and the mole ratio of primary amine to thiophosphoryl chloride is typically in the range of about 0.95 to about 1.1 moles of amine per mole of the $PSCl_3$. For best results, the mole ratio of primary amine to thiophosphoryl chloride is in the range of about 1.00 to about 1.05 moles of amine per mole of the $PSCl_3$.

The desired product of the first stage reaction is an N-hydrocarbylaminothiophosphoryl dichloride. Such compounds have the formula, $(H)(R)N—P(=S)Cl_2$, where R is a hydrocarbyl group.

As noted above, primary hydrocarbyl monoamine and tertiary amine are charged to the first reaction chamber as a preformed mixture which also includes one or more solvents, and the proportions of primary hydrocarbyl monoamine and tertiary amine in such preformed mixture are typically in a molar ratio range of about 1:1 to about 1:1.5 respectively. Typically, the proportions of such preformed mixture and the thiophosphoryl chloride fed to the first reaction chamber are such that per mole of thiophosphoryl chloride there are in the range of about 0.95 to about 1.1 moles of primary hydrocarbyl monoamine and in the range of about 0.95 to about 1.5 moles of tertiary amine.

In the second stage reaction between the N-hydrocarbylaminothiophosphoryl dichloride and ammonia, one or more temperatures in the range of about 5° to about 50° C. and one or more pressures in the range of about 15 to about 100 psig are typically employed, with the proviso that in any given situation, the temperature is high enough to keep the co-product ammonium chloride-ammonia complex in solution, yet low enough to avoid significant reduction in yield (e.g., a loss of more than 5 wt % yield) of N-hydrocarbylthiophosphoric triamide. The N-hydrocarbylthiophosphoric triamides have the formula, $(H)(R)N—P(=S)(NH_2)_2$, where R is a hydrocarbyl group. Preferred conditions for the second stage reaction, especially when producing N-n-butylthiophosphoric triamide involve one or more temperatures in the range of about 8° to about 15° C. and one or more pressures in the range of about 25 to about 40 psig. In the second stage reaction the proportions of ammonia to the N-hydrocarbylaminothiophosphoryl dichloride are such that there are at least about 16 moles of ammonia, and preferably at least about 20 moles of ammonia, per mole of N-hydrocarbylaminothiophosphoryl dichloride. In theory there is no upper limit on the amount of ammonia used as the excess ammonia does not materially interfere with the desired reactions. Thus the amount of excess ammonia above the foregoing minimum amounts is largely a matter of common sense and practicality; i.e., the larger the excess, the larger the amounts of ammonia that need to be recovered and recycled.

The amount of solvent used in the process is an amount sufficient to provide a suitably fluid reaction medium, and thus is largely a matter of choice, common sense, and practicality. Thus unduly excessive amounts of solvent should be avoided as the larger the amount used, the larger the amount that needs to be recovered and recycled.

The first stage and the second stage reactions are both exothermic reactions and thus suitable equipment should be provided to ensure that adequate cooling capacity is available for each of the two stages. In a preferred embodiment, the heat of reaction from the first stage reaction mixture is removed by continuously circulating a portion of that reaction mixture from the first stage reaction chamber into a heat exchanger where heat is removed by a cooling medium, and thence back to the first reaction chamber. In a particularly preferred embodiment the heat of reaction from the first stage reaction mixture is removed by controlling the pressure such that the reaction mixture boils and the vapors from the boiling mixture are condensed in a dephlegmator heat exchanger and refluxed back to the first reaction chamber.

In a preferred embodiment, the reaction mixture in the first reaction chamber is continuously stirred or agitated by a mechanical stirrer or agitator, and the preformed mixture and the thiophosphoryl chloride are both fed into such reaction mixture below the surface thereof and in close proximity to the stirrer/agitator to ensure prompt and rapid mixing of these feeds.

In still another preferred embodiment, the heat of reaction from the second stage reaction mixture is removed by continuously circulating a portion of that mixture through a heat exchanger and thence back to the second reaction chamber.

Alternatively, the first and the second reaction chambers are both heat exchangers that provide a residence time in the range of 1 to about 10 minutes and that provide sufficient heat exchange surface in contact with the reaction mixture therein to enable removal of the heat of reaction generated within such residence time.

Effluent from the second reaction chamber is withdrawn at a rate sufficient to maintain a substantially constant volume of reaction mixture in the second reaction chamber, and preferably, the effluent from the first reaction chamber is withdrawn therefrom and fed to the second reaction chamber at a rate that maintains a substantially constant volume of reaction mixture in the first reaction chamber.

Preferably, the effluent from the second reaction chamber is caused/allowed to separate into (A) an inorganic phase comprising predominately ammonia, ammonium chloride and co-product thiophosphoric triamide, and (B) an organic phase comprising predominately N-hydrocarbylthiophosphoric triamide, tertiary amine, solvent and dissolved ammonia, and the resultant phases are separated from each other. This is preferably accomplished by allowing the effluent to stand in a quiescent state for a suitable period of time for the distinct separate phases to form and then draining off the lower layer. Other separation techniques such as siphoning off the top layer, use of emulsion breakers, and like procedures can be used whenever deemed necessary or desirable. After effecting this separation, it is preferred to separate ammonia along with a portion of the solvent from the isolated organic phase, and compress and cool this ammonia-solvent mixture to form a recycle mixture of liquid ammonia and solvent. This separation also provides as the residual mixture, a concentrated product mixture comprising predominately N-hydrocarbylthiophosphoric triamide, and residual solvent and tertiary amine. The recycle mixture of ammonia and the solvent remaining therewith is recycled for use as a portion of the ammonia feed to the second reaction chamber.

The concentrated product mixture is then processed so as to separate and recover tertiary amine and solvent therefrom, and the tertiary amine and solvent collected therewith are recycled for use as a portion of the feed for making the preformed mixture to be fed to the first reaction chamber. The residual portion of the organic phase remaining after this separation comprises N-hydrocarbylthiophosphoric triamide, and only small residual amounts of solvent and tertiary amine. Thereupon the N-hydrocarbylthiophosphoric triamide and the small residual amounts of solvent and tertiary amine are separated from each other to yield a purified N-hydrocarbylthiophosphoric triamide product. Either or both of this separated residual solvent and tertiary amine is/are recycled for use as a portion of the feed for making the preformed mixture fed to the first reaction chamber.

Except for the gravity separation of the N-hydrocarbylthiophosphoric triamide organic phase and the ammonium chloride inorganic phase wherein draining, decantation, or like physical separation technique is used, the specific techniques used for effecting the other separations will depend to some extent upon the identities of the materials making up the mixtures being processed. Usually distillations or flash distillations will be employed whenever this is feasible. However, in any case where such distillation procedures are not feasible because of the properties of the materials being processed, recourse may be had to other separation techniques such as solvent extraction procedures, chromatographic separation procedures, or the like.

First Stage Reaction. Referring now to the embodiment depicted in FIGS. 1 and 2, triethylamine (TEA) and tetrahydrofuran (THF) are fed to the first reactor 10 as a mixture from a recycle solvent tank 12. Make-up THF and TEA stored in tanks 14 and 16, respectively, are added to recycle tank 12 as needed to maintain a constant solvent composition going to reactor 10. The feed rate is determined by maintaining a constant feed ratio of TEA to $PSCl_3$, based on periodic analyses of TEA in the TEA/THF mixture. This analysis should have ±400 ppm (or better) resolution to allow control of the $TEA/PSCl_3$ mole ratio within 1–2% of target (1.10±0.02). TEA is consumed in this first reaction step and regenerated in the second reaction, while THF acts only as a solvent.

In first reactor 10, $PSCl_3$ (mass flow controlled) is reacted with n-butylamine (NBA) to form N-n-butylaminothiophosphoryl dichloride (BATPD) intermediate. The NBA is stored in tank 20 under nitrogen. Two different streams are fed to the reactor: 1) neat $PSCl_3$ from tank 18; and 2) mixed feeds of recycle THF/TEA and NBA from static mixer 22. The NBA feed rate is proportioned to the $PSCl_3$ feed rate to maintain a mole ratio of approximately 1.01 moles of NBA per mole of $PSCl_3$ and the THF/TEA feed rate is proportioned to the $PSCl_3$ feed rate to maintain a mole ratio of approximately 1.10 moles of TEA per mole $PSCl_3$.

Mixing is considered highly important for achieving very high efficiency in this reaction, and thus the NBA and THF/TEA are combined in static mixer 22 upstream of the reactor, and introduced to the reactor through a dip leg just above the agitator. The $PSCl_3$ is fed neat through a separate dip leg into the same area of the reactor. The HCl formed as co-product reacts with the TEA to form a TEA.HCl salt which precipitates from the reaction mass.

The reaction to form this intermediate BATPD is very exothermic, and most of this heat of reaction is removed by refluxing the THF solvent in a dephlegmator 24. Recommended reaction conditions in reactor 10 are 0–15° C. and, to allow solvent reflux, about 40–70 mm Hg (0.8–1.4 psia) pressure. Feed rates are adjusted to provide a three hour residence time in reactor 10. Since this reaction is very fast (1–2 minutes maximum) and irreversible, holdup in this reactor simply provides surge capacity for the process. Additional cooling for the reaction is provided by the reactor jacket and a pump-around loop through heat exchanger 26. The reaction mass discharge is fed continuously to the second reactor 30 via level control on first reactor 10.

Second Stage Reaction. In the second reactor 30, the intermediate BATPD from reactor 10 reacts with ammonia to give the final product, N-(n-butyl)thiophosphoric triamide (BTPT). The HCl generated by the reaction also reacts with ammonia to form ammonium chloride, and the TEA.HCl also reacts with ammonia to liberate the TEA and form additional ammonium chloride. A total of 5 moles of ammonia per mole BATPD is consumed in this step. This reaction is very exothermic, and the heat of reaction is removed via a pump-around loop through heat exchanger 32. Reaction conditions for reactor 30 are 8°–15° C. and 25–38 psig, and the residence time is about 90 minutes.

Ammonia is fed by pressure control to reactor 30, and the ammonia feed consists of the recycle stream from product phase column 33 and fresh ammonia from storage vessel 34. A total of about 23–25 moles of ammonia per mole of BATPD is fed to reactor 30. Of this, about 14 moles is fresh ammonia. In order to keep the ammonium chloride co-product in solution, this amount of excess ammonia is used so that the ammonium chloride and the ammonia form a separate liquid phase containing about three moles of ammonia per mole of ammonium chloride. At lower ammonia levels, the ammonium chloride precipitates from the solution, forming a slurry which tends to cause pluggage problems. If the temperature in reactor 30 is allowed to go below 6° C., the ammonium chloride/ammonia complex ($NH_4Cl.3NH_3$) will precipitate, which can also cause pluggage problems. Effluent discharge from this reactor is controlled to maintain constant level in reactor 30, and is sent to phase separator 36.

Phase Separation. The reaction mass coming from reactor 30 separates into two phases in phase separator 36, namely, (A) an inorganic phase containing ammonia, ammonium chloride, most of the by-product thiophosphoric triamide (TPT), and small amounts (<1%) of BTPT, THF and TEA; and (B) an organic phase containing THF, TEA, BTPT, some of the TPT, the other phosphorus by-product impurities, and ammonia. These are separated by gravity in separator 36 by employing a residence time therein of approximately 45 minutes. The separated phases are then stored, respectively, in two vessels, vessel 38 for the organic phase mixture and vessel 40 for the inorganic phase mixture. All three of these vessels (separator 36, and vessels 38 and 40) are maintained at the same pressure (40–50 psig) to allow gravity flow, and are cooled to hold a constant temperature (and thus constant composition and pressure). In the preferred system depicted, make-up ammonia can be fed directly to any of these drums from storage vessel 34, if the ammonia concentration becomes low enough to cause ammonium chloride precipitation.

Organic Phase Distillation. The organic phase from vessel 38 is first distilled in product phase column 33 to remove dissolved ammonia and most of the solvents, i.e., THF and TEA. The ammonia stream (which contains about 25% THF) is recycled directly to the second stage reaction in reactor 30; the combined THF and TEA solvents are taken as a vapor side-stream from the column sump, condensed in condenser 35, and transferred via pump 37 to recycle solvent tank 12. The concentrated (bottoms) product solution (containing about 50% THF) is transferred to feed drum 42.

Column 33 is operated at about 7–8 psia pressure and 55° C. bottoms temperature to minimize thermal decomposition of the product. Built into the upper portion of column 33 is column dephlegmator condenser 46 which is used to cool the vapor and condense most of the THF as internal reflux. Two 2-stage blowers, 48 and 50 compress the ammonia vapor sufficiently (about 35 psig) to allow condensation and cooling with refrigerated Dowtherm® J coolant. This liquid ammonia/THF stream is then routed directly back to reactor 30.

Inorganic Phase Dilution. Typically, the inorganic phase (chiefly composed of ammonia and ammonium chloride) is first diluted with water and stored in storage tank 56, analyzed, and batch transferred to a railcar 58 prior to shipment. Preferably, the water added is proportioned to yield a co-product solution containing about 25% water, about 38% dissolved ammonium chloride and about 37% ammonia, which is a useful industrial product mixture. In order to suit specific industrial uses for the ammonia and ammonium chloride co-products, the amount of water added can be varied, and in fact, the addition of water can be entirely eliminated if desired. The foregoing aqueous co-product solutions are the solutions with which are blended the corrosion inhibitors of this invention.

Wiped-film Evaporation, Nitrogen Strip and Optional Dilution. The concentrated BTPT/THF/TEA solution from feed drum 42 is fed (by flow control) to wiped-film evaporator 44, to remove most of the remaining THF and TEA solvents. Wiped-film evaporator 44 is operated at about 110 mm Hg absolute and 95° C., producing a bottoms product containing <2% residual solvents. The solvent vapors from wiped-film evaporator 44 are condensed in heat exchanger 62, and the condensed solvent is recycled to recycle solvent tank 12 via pump 64. The bottoms product (predominately BTPT) from wiped-film evaporator 44 is fed (by level control on the bottoms receiver pot and pump 66) directly to the upper portion of nitrogen stripping column 68, in which hot nitrogen (about 65° C., atmospheric pressure) is passed upwardly in countercurrent flow to the down-flow product stream to further reduce the small residual solvent content of the BTPT to about 0.5% maximum. This neat product stream is then gravity fed into storage vessel 70 in which, if desired, it can be mixed with one or more solvents for storage and ultimate shipment.

As described in commonly-owned copending U.S. application Ser. No. 08/786,535, filed Jan. 21, 1997, all disclosure of which is incorporated herein by reference, it is highly advantageous to use a wiped-film evaporator operated at a suitable temperature in the range of about 60° to about 140° C., and at a suitable pressure higher than about 40–200 torr absolute (preferably about 100° to about 130° C. at 50–150 torr absolute) for separating most of the remaining solvents from the BTPT/THF/TEA solution. Use of wiped-film evaporator operated under such suitable conditions avoids solids formation on the heating surface of the wiped-film evaporator, and successfully overcomes problems associated with the recovery of N-alkylthiophosphoric triamides from tetrahydrofuran-triethylamine solutions, especially thermal degradation of the triamide product, while at the same time providing a separation process which not only is ideally-suited for large scale commercial operation but which, in addition, actually improves the efficiency of the product recovery step itself.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. An aqueous ammoniate solution made during the manufacture of N-hydrocarbyl thiophosphoric triamides, consisting essentially of an aqueous solution of ammonium chloride and ammonia containing at least one water-soluble sulfur-containing impurity normally tending to engender corrosion of ferrous metal, said solution additionally having dissolved therein a ferrous metal corrosion-inhibiting amount of at least one water-soluble oxide of zinc, aluminum, arsenic, antimony or bismuth; wherein the aqueous ammoniate solution is predominantly inorganic, and is separated from an organic phase containing N-hydrocarbyl thiophosphoric triamides during the manufacture of said N-hydrocarbyl thiophosphoric triamides.

2. A solution according to claim 1 wherein the oxide that is dissolved in said solution is one or more of zinc oxide, aluminum oxide, or bismuth oxide.

3. A solution according to claim 1 wherein the oxide that is dissolved in said solution is zinc oxide.

4. A solution according to claim 1 wherein the oxide that is dissolved in said solution is aluminum oxide.

5. A solution according to claim 1 wherein the oxide that is dissolved in said solution is bismuth oxide.

6. A process which comprises:
   a) mixing and reacting a hydrocarbyl primary amine and thiophosphoryl chloride in at least one liquid inert organic solvent and in the presence of tertiary amine to complex with the HCl formed in the reaction, to produce a reaction mixture containing N-hydrocarbylaminothiophosphoryl dichloride;
   b) mixing and reacting ammonia and at least a portion of the reaction mixture formed in a) in proportions (1) that are at least about 16 moles of ammonia per mole of N-hydrocarbylaminothiophosphoryl dichloride, (2) that produce a reaction mixture containing N-hydrocarbylthiophosphoric triamide, and (3) that keep in solution substantially all of the ammonium chloride co-product formed in the reaction, and maintaining the temperature of the reaction mixture high enough to keep ammonium chloride-ammonia complex from forming an appreciable amount of solid phase in said reaction mixture, but low enough to avoid significant reduction in yield of N-hydrocarbylthiophosphoric triamide;
   c) allowing/causing the reaction mixture of b) to form an anhydrous predominately inorganic liquid phase comprising (i) ammonia and ammonium chloride and/or (ii) a product or complex thereof, and a separate anhydrous predominately organic liquid phase comprising N-hydrocarbylthiophosphoric triamide and said solvent;
   d) separating said phases from each other; and
   e) converting at least a portion of the separated predominately inorganic liquid phases into a corrosion-inhibiting aqueous solution thereof by adding to the water used in forming such solution or by adding to said solution after it has been formed, a ferrous metal corrosion-inhibiting amount of at least one water-soluble ferrous metal corrosion inhibitor selected from a salt or an oxide of zinc, aluminum, arsenic, antimony or bismuth.

7. A process according to claim 6 wherein the salt or oxide that is blended with said solution is one or more of the following: zinc oxide, a zinc dihalide, aluminum oxide, an aluminum trihalide, bismuth oxide.

8. A process according to claim 6 wherein the salt or oxide that is blended with said solution is zinc oxide.

9. A process according to claim 6 wherein the salt or oxide that is blended with said solution is a zinc dihalide.

10. A process according to claim 6 wherein the salt or oxide that is blended with said solution is aluminum oxide.

11. A process according to claim 6 wherein the salt or oxide that is blended with said solution is an aluminum trihalide.

12. A process according to claim 6 wherein the salt or oxide that is blended with said solution is bismuth oxide.

13. A process according to claim 6 wherein the salt or oxide that is blended with said solution is one or more of $ZnO$, $ZnCl_2$, $Al_2O_3$, $AlCl_3$, or $Bi_2O_3$.

14. A process according to claim 6 wherein said hydrocarbyl primary amine in a) is n-butylamine.

15. A process which comprises:
   a) continuously feeding to and mixing in a first reaction chamber (i) a preformed mixture of primary hydrocarbyl monoamine, tertiary amine and at least one liquid inert organic solvent, and (ii) thiophosphoryl chloride and removing heat of reaction at a rate sufficient to maintain the temperature of the reaction mixture in the range of about $-20°$ to about $+50°$ C., to produce a reaction mixture containing N-hydrocarbylaminothiophosphoryl dichloride;
   b) continuously feeding and mixing in a second reaction chamber (i) an effluent stream of reaction mixture formed in the first reaction chamber which effluent is withdrawn at a rate to maintain a substantially constant volume of reaction mixture in the first reaction chamber, and (ii) ammonia in proportions (1) that are at least about 16 moles of ammonia per mole of N-hydrocarbylaminothiophosphoryl dichloride, (2) that produce a reaction mixture containing N-hydrocarbylthiophosphoric triamide, and (3) that keep in solution substantially all of the ammonium chloride co-product formed in the reaction, and removing heat of reaction from the mixture formed in b) at a rate of removal such that the temperature of the reaction mixture remains high enough to keep ammonium chloride-ammonia complex from forming an appreciable amount of solid phase in said reaction mixture, but low enough to avoid significant reduction in yield of N-hydrocarbylthiophosphoric triamide;
   c) withdrawing effluent from the second reaction chamber at a rate sufficient to maintain a substantially constant volume of reaction mixture in the second reaction chamber;
   d) enabling/causing the effluent from c) to separate into a predominately inorganic liquid phase comprising predominately ammonia, ammonium chloride and co-product thiophosphoric triamide, and a predominately organic liquid phase comprising predominately N-hydrocarbylthiophosphoric triamide, tertiary amine, solvent and dissolved ammonia;
   e) separating the resultant phases from each other; and
   f) converting at least a portion of the separated predominately inorganic liquid phase into a corrosion-inhibited aqueous solution thereof by adding to the water used in forming such solution or by adding to said solution after it has been formed, a ferrous metal corrosion-inhibiting amount of at least one water-soluble ferrous metal corrosion inhibitor selected from a salt or an oxide of zinc, aluminum, arsenic, antimony or bismuth.

16. A process according to claim 15 wherein said primary hydrocarbyl monoamine in a) is a monoalkyl monoamine.

17. A process according to claim 16 wherein said monoalkyl monoamine is n-butylamine.

18. A process according to claim 15 wherein in a):
said primary hydrocarbyl monoamine is a monoalkyl monoamine, said tertiary amine is a triakylamine, and said inert organic solvent is a cyclic ether.

19. A process according to claim 18 wherein said monoalkyl monoamine is n-butylamine, said triakylamine is triethylamine, and said cyclic ether is tetrahydrofuran.

20. A process according to claim 15 wherein said corrosion inhibitor that is added to said solution in f) is $Al_2O_3$ or $AlCl_3$.

* * * * *